United States Patent [19]

Taylor

[11] Patent Number: 4,907,599
[45] Date of Patent: * Mar. 13, 1990

[54] SOFT TISSUE CORE BIOPSY INSTRUMENT

[75] Inventor: Glenn N. Taylor, Longmont, Colo.

[73] Assignee: Hart Enterprises, Inc., Wyoming, Mich.

[*] Notice: The portion of the term of this patent subsequent to Nov. 21, 2006 has been disclaimed.

[21] Appl. No.: 231,907

[22] Filed: Aug. 15, 1988

Related U.S. Application Data

[63] Continuation-in-part of Ser. No. 150,984, Feb. 1, 1988, Pat. No. 4,821,551.

[51] Int. Cl.⁴ ............................................. A61B 10/00
[52] U.S. Cl. ..................................... 128/754; 128/305
[58] Field of Search .......... 128/305, 310, 749, 751-754

[56] References Cited

U.S. PATENT DOCUMENTS

| | | | |
|---|---|---|---|
| 4,600,014 | 7/1986 | Beraha | 128/754 |
| 4,669,154 | 10/1987 | Lindgren | 128/754 |
| 4,776,346 | 10/1988 | Beraha et al. | 128/754 |

FOREIGN PATENT DOCUMENTS

| | | | |
|---|---|---|---|
| 0010321 | 4/1980 | European Pat. Off. | 128/754 |
| 8701097 | 11/1987 | World Int. Prop. O. | 128/754 |

*Primary Examiner*—Max Hindenburg
*Assistant Examiner*—Randy Citrin
*Attorney, Agent, or Firm*—Thomas R. Vigil

[57] ABSTRACT

The soft tissue core biopsy instrument comprises a proximal outer barrel member and a distal inner barrel member which is slidably received within the outer barrel member. A cannula driver is slidably received within the distal inner barrel member and has a distally extending cannula fixed thereto. A stylet extends distally from a stylet hub with a stylet hub being removably attached to the proximal outer barrel member. A spring is positioned within the inner barrel member between a proximal wall thereof and a proximal wall of the cannula driver for biasing the cannula driver forwardly and a latching mechanism for latching the cannula driver in a proximally retracted position against the action of spring is also provided. A trigger for unlatching the latching mechanism may be actuated to allow the spring to quickly return to its forwardly biased position, shooting or forcing the cannula driver to a distally extended position, projecting the cannula over said stylet.

13 Claims, 6 Drawing Sheets

SOFT TISSUE CORE BIOPSY INSTRUMENT

The present application is a continuation-in-part of application Ser. No. 07/150,984 filed on 2/1/88, U.S. Pat. No. 4,881,551.

BACKGROUND OF THE INVENTION

1. Field of the Invention

The present invention relates to a soft tissue core biopsy instrument which is semi-automatic in operation. More specifically, the biopsy instrument of the present invention provides an instrument which can be operated using only one hand and which includes a cutting cannula which is caused to move in a snap action over a stylet which is manually advanced.

2. Description of the Prior Art

Heretofore, various soft tissue core biopsy instruments have been proposed.

The most well known instrument used in this procedure is manufactured by Travenol Laboratories of Deerfield, Ill. and is sold under the mark "TRU-CUT". This instrument enjoys 98% of the existing market. As disclosed in U.S. Pat. No. 3,477,423, the instrument comprises a two piece assembly; an outer cutting cannula mounted to one hub member and an inner stylet with a sampling notch ground into it mounted to a second hub, with the hubs being slidably interlocked. The instrument is assembled and placed into the body with the outer cutting cannula just to the rear of a lancet point or bevelled distal end of the stylet. Upon inserting the device up to or in front of the area to be biopsied, advancement of the assembly is halted. The stylet is manually advanced distally of the cannula with the cannula held stationery. Upon advancement of the stylet, the specimen notch is exposed. Tissue surrounding the stylet contracts into the specimen notch and the cutting cannula is then manually advanced distally over the stylet, slowly shearing off the tissue entrapped in the stylet's specimen notch. The instrument is then either (a) withdrawn and the stylet advanced distally to expose the tissue for preparation for study or (b) left in place and only the stylet is proximally removed from within the cannula so a determination of successful sampling may be made. If the sampling was not successful, the stylet may be reinserted into the cannula, which remains positioned within the patient, and a attempt to reposition the assembly of stylet and cannula and repeat sampling can be made.

Such technique using this basic design of a biopsy instrument is referred to as a manual technique. One drawback to the manual technique is that it requires a great deal of manual dexterity and motor coordination, along with the use of both hands, to advance the stylet while maintaining the position of the cannula and then to maintain the position of the stylet while advancing tee cannula.

Another drawback is that the canula is advanced relatively slowly, resulting in an extremely poor cutting action and allowing the surrounding tissue an opportunity to collapse, thus making no use of the stored kinetic energy in the material being severed.

The Beraha U.S. Pat. No. 4,600,014 discloses a transrectal prostate biopsy device which comprises a handle held in a physician's palm, an a guide tube extending forwardly of the handle. A cannula is slidably disposed within the guide tube and is movable from within the guide tube forwardly out of the distal end of the guide tube. A sampling stylet is telescopically disposed within the cannula and projects from the rear of the handle. A knob is provided at the proximal end of the stylet for extending a distal end of the stylet out of the distal end of the guide tube to expose a sampling thereon. The physician holds the handle in one hand using his index finger at the distal end of the guide tube to guide the instrument to a selected transrectal point on the prostate. Upon locating the point, the one hand holds the instrument steady while the other hand pushes the stylet forward and then pushes the cannula over the stylet to sever the tissue within the sampling slot. The device is then withdrawn to gain access to the sample. In one embodiment of the device, the cannula, when in the retracted position, is spring loaded by means of a compressed spring. A release lever, which works against the compressed spring can be activated to release compression of tee spring which then expands and pushes the cannula outwardly over the stylet.

This instrument, as stated, requires two handed operation. Also, since the stylet is not removable proximally from within the handle, the entire instrument must be withdrawn to obtain access to the sample.

Within the last two years, a fully automatic instrument manufactured by Radiplast, Inc. of Sweden has been introduced and described in U.S. Pat. No. 4,699,154. This instrument comprises a reusable, spring-loaded box-shaped housing or handpiece, which activates a disposable cannula and stylet set. Both the stylet and cannula are activated in rapid succession.

The instrument has the advantage of eliminating the dexterity and motor coordination necessary in use of manual devices and also eliminates the slow cutting action of the manually advanced cannula and replaces it with a very quick, clean cut. This instrument, however, also has its drawbacks.

First, the reusable handpiece is very large, heavy, cumbersome, and expensive. Its weight and the awkwardness in using same preclude it from being used with imaging equipment other than ultrasound, inasmuch as it must be inserted into the body with the user maintaining control of the handpiece at all times. Thus, the patient cannot be imaged with many conventional radiographic apparatus, such as CAT scanners. A further drawback is encountered in automatically activating both the stylet and the cannula, as opposed to activating the stylet manually, in that the rapid speed at which the cannula follows the stylet into the tissue does not allow much tissue to collapse into the specimen notch, limiting the size of the sample.

Also, it does not allow imaging of the device with the stylet and sampling notch in the actual tissue to be sampled and further, since a handpiece is utilized, the user cannot remove the stylet proximally from within the instrument to inspect the sampling and the entire instrument must be removed to obtain access to the sampling, so that, if a repeat sampling is required, the entire instrument must be reinserted. Also, since the handpiece is reusable, additional costs above the purchase price are involved in cleaning, maintenance, and maintaining sterility of the handpiece.

The semi-automatic soft tissue core biopsy instrument of the present invention, as will be described in greater detail hereinafter, is completely disposable, lightweight and inexpensive. Further, it allows the user to advance the stylet manually, and then rapidly advance the cutting cannula automatically, all with one hand. Also, since the stylet is removable from the proximal end of the instrument, the position of the cannula within the body need not be disturbed if a repeat biopsy is required.

SUMMARY OF THE INVENTION

According to the invention there is provided a soft tissue core biopsy instrument comprising:
  a proximal outer barrel member having a distal end and a proximal end;
  a distal inner barrel member which is slidably received within said outer barrel member and which has a distal end and a proximal end;
  a cannula driver in said inner barrel member;
  a cannula extending distally from said inner barrel member, being fixed to said cannula driver, and having a distal tip, said cannula driver being slidably received and movable within said distal inner barrel member and said cannula extending a predetermined distance out of said distal end of said inner barrel member when the instrument is in an at rest condition;
  a stylet having a distal end, a distal end portion, a proximal end, and being removably received in said outer barrel, in said inner barrel, and in said cannula, said distal end portion having a biopsy sample receiving notch therein;
  a stylet hub mounted to said proximal end of said stylet, said stylet hub being removable attached to the proximal end of said proximal outer barrel member to enable multiple biopsies to be obtained with one insertion of said cannula,
  said stylet extending distally from said hub and within said cannula with said distal end portion (a) positioned within said cannula when the instrument is in an at-rest position and (b) extending distally of said distal tip of said cannula in position to capture a biopsy sample when the instrument is in a cocked position.
  biasing means within said inner barrel member for biasing said cannula driver toward the distal end of said inner barrel member;
  latching means associated with said cannula driver and said inner barrel member for latching said cannula driver in a proximally retracted cocked position within said outer barrel member and said inner barrel member against the biasing action of said biasing means;
  a trigger, associated with said latching means, for unlatching said latching means, said trigger, upon being actuated for unlatching of said latching means, allowing said biasing means to quickly return said cannula driver and said cannula to said at rest distally extending position thereof and over said stylet distal end portion.

The cannula driver biasing means comprise a spring located within said inner barrel member between a proximal wall of said inner barrel member and a proximal end of said cannula driver.

DESCRIPTION OF THE PREFERRED EMBODIMENTS

Figure 1:
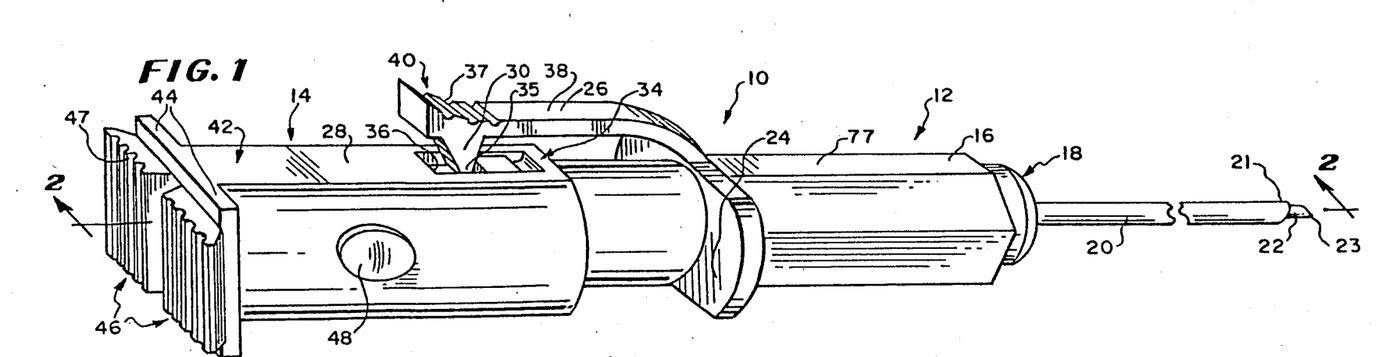
FIG. 1 is a perspective side view of the biopsy instrument of the present invention in an at-rest condition.

Referring now to the drawings in greater detail, there is illustrated in FIG. 1 the semi-automatic soft tissue core biopsy instrument 10 of the present invention.

As illustrated, the instrument 10 is syringe-like and has a distal, inner barrel member 12 an a proximal, outer barrel member 14. At a distal end 16 of inner barrel member 12 is a nose or plug 18. Extending through and distally of the plug 18 is a hollow cannula 20 having a pointed distal end 21 and having a stylet 22, also having a pointed end 23, therein. The pointed ends 21 and 23 are oppositely directed.

The inner barrel member 12 also has two outwardly extending finger flanges 24 approximately centrally along its length, each flange 24 being on an opposite side of the instrument 10. The flanges are formed integrally with the inner barrel member 12.

The inner barrel member 12 further has an integral lever arm 26 extending upwardly therefrom and proximally over an upper surface 28 of the proximal outer barrel member 14. The lever rm 26 originates at a position corresponding to the position of the finger flanges 24 along the length of the barrel member 12 and terminates at a position where a downwardly extending V-shaped trigger element 30 thereof can coact with a latching mechanism 32 as will be described in greater detail hereinafter. Latching indicator structure 34 is cut into the top surface 28 of the proximal outer barrel member 14.

The lever arm 26 is formed in such a manner as to be downwardly biased, with a downwardly directed detent 35 of the V shaped trigger element 30 resting within a cutout 36 of the latching indicator structure 34 when the instrument 10 is in an at rest condition.

Serrations 37 are provided along a top surface 38 of the arm 26 along a proximal end section 40 of the arm 26.

The outer barrel member 14, incorporating the latching indicator structure 34 for the trigger element 30 also has, extending laterally outwardly along a proximal end 42 thereof a rear flange 44 against which a pair of wings 46 rest. The wings 46 are serrated along a proximally facing end face 47 thereof and will be described in greater detail in connection with the description of FIGS. 8 and 9.

At least one, and preferably two, pins 48, are provided for maintaining the various components of the instrument 10 unitary and for maintaining the components against relative rotation. Such rotational position of the components must be maintained to keep the pointed end 21 of the cannula 20 in opposite alignment with the pointed end 23 of the stylet 22, as will be described hereinafter.

Figures 2, 3, 4:
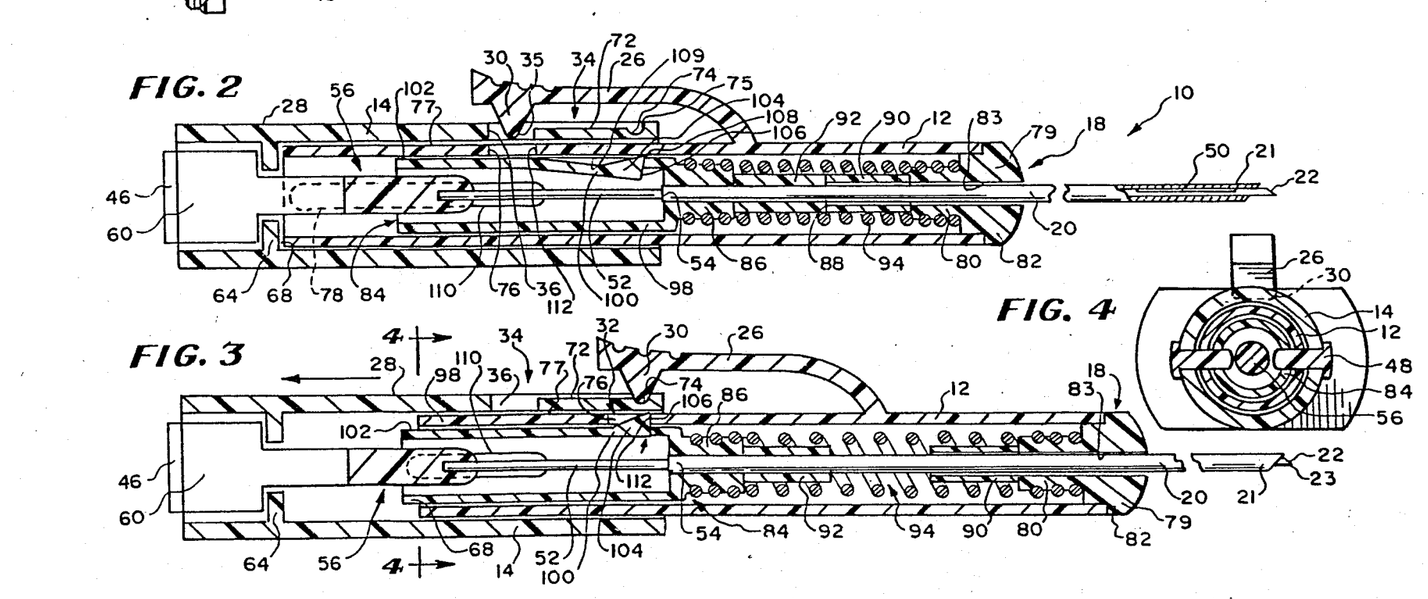
FIG. 2 is a longitudinal cross sectional view through the instrument and is taken along line 2—2 of FIG 1.
FIG. 3 is a longitudinal cross sectional view similar to FIG. 2 and shows a cannula driver of the instrument being proximally biased.
FIG. 4 is a radial cross sectional view through the instrument and is taken along line 4—4 of FIG. 3.

Illustrated in FIG. 2 is a longitudinal cross sectional side view through the instrument 10 and shows the position of the various components of the instrument 10, when the instrument 10 is in an at rest condition.

The stylet 22 is now seen to have an upwardly facing sampling notch 50 ground therein at a distal position thereon, just behind the pointed tip 23 thereof. The notch 50, when the instrument 10 is at rest, is located just inside the pointed tip 21 of the cannula 20. A proximal end 52 of the stylet 22 exits a proximal ed 54 of the cannula 20 and extends a predetermined distance proximally where it is fixed within a hub 56 for the stylet 22.

The hub 56 is somewhat T shaped nd has a proximal end portion 60 which is increased in diameter.

The outer proximal barrel member 14 also has an inwardly extending circumferential rib 64 which limits distal insertion of the hub 56 into the proximal outer barrel member 14 by abutment against the increased in diameter portion 60 of the hub 56. Further, the rib 64 also forms a stop 64 which limits proximal motion of the inner barrel member 12 within the outer barrel member 14 by abutting against a rear or proximal end edge 68 of the inner barrel member 12.

As stated above, the outer barrel member 14 includes the latching indicator structure 34 for the trigger element 30 of the instrument 10. The latching indicator structure 34 includes the cutout 36 which extends through the thickness of outer barrel member 14 at a position along the upper surface 28 such that the detent 35 of the trigger element 30 rests within the cutout 36 when the instrument 10 is in an at-rest condition.

Distal to the cutout 36 is a small, reduced in thickness area 72 of upper wall 28 which terminates distally in a groove 74, with a distal end wall 75 of the groove 74 returning to the thickness of the outer barrel member 14. The detent 35 of the trigger 30, as will be described hereinafter, can be slid distally and proximally within the latching indicator structure 34.

The inner barrel member 12 also has a full thickness cutout 76 in an upper surface 77 thereof which is aligned directly beneath the cutout 36 in the proximal outer barrel member 14 when the instrument 10 is in an at-rest condition.

Further, to provide for limited slidability of the inner barrel member 12 within the outer barrel member 14, even though they are maintained unitary by the pins 48, elongate longitudinal lateral slots 78 (shown in phantom) are provided in the inner barrel member 12 for receiving the pins 48 therein, thus allowing limited relative longitudinal movement between the inner barrel member 12 and the outer barrel member 14.

Turning now to the plug 18 at the distal end 16 of the inner barrel member 12, the plug 18 has a somewhat mushroom shape, a head portion 79 thereof fitting snugly within the barrel member 12 and having a first inwardly stepped proximal portion 80 extending proximally within the barrel member 12. The head portion 79 also has, along its distal end, an outwardly extending flange 2 which has a diameter equal to the diameter of the inner barrel member 12 to provide a smooth slightly rounded distal end 16 to the inner barrel member 12. The plug 18 also has a central longitudinal bore 83 through which the cannula 20 slidably extends.

The inner barrel member 12 further incorporates a slidable, somewhat Y shaped in cross section cannula driver 84. A first inwardly stepped distal end portion 86 of the cannula driver 84, forming part of the tail of the Y, extends distally within the inner barrel member 12. The first stepped end portions 80 and 86 are equal in size and diameter and are threaded. A second inwardly stepped portion 90 extends proximal of stepped end portion 80 of the plug 18 and a second inwardly stepped portion 92 extends distally of stepped end portion 86 of the cannula driver 84. A spring 94 is threadedly fixed, at one end, over and to the first stepped portion 80 of the plug 18 and at its other end over and to the first stepped portion 86 of the cannula driver 84. When the instrument 10 is in an at-rest position, the spring 94, is contracted. The second stepped portions 90 and 92 are loosely received within the remaining central coils of the spring 94 and abut one another, the portions 90 and 92 being maintained in abutting relationship by the contracted spring 94 when the instrument 10 is in an at rest condition. The second stepped portions 90 and 92 serve to limit distal motion of the cannula driver 84 within barrel member 12, as will be described hereinafter.

The cannula driver 84 also has an elongate cylindrical proximally extending body portion 98 which has a diameter almost equal to an inner diameter of the distal inner barrel member 12, providing for slidability of the cannula driver 84 within the inner barrel member 12.

This body portion 98 has a distally terminating flap 100 cut through a precise area of its thickness along an upper surface 102 thereof. The flap 100 has a conically, distally radially outwardly flanged distal end portion 104. The end portion 104 terminates in a thick, vertical distal end wall 106. As shown, when the instrument 10 is in an at rest condition, the end portion 104 of the flap 100 is flexed inwardly into the body portion 98, with a top end edge 108 of the vertical distal end wall 106 bearing against the inner surface 109 of the inner barrel member 12, at a position distal to the position of the cutout 76 in the inner barrel member 12. The necessity for precise positioning of the flap 100 will be further described in connection with the description of FIG. 3, however, here it is to be noted that the groove 74 of the latching indicator structure 34 is positioned directly above the distal end portion 104 of the flap 100 when the instrument 10 is in an at rest condition.

The cannula driver 84 is also maintained integral within the instrument 10 by the pins 48 and, since the cannula driver 84 must be limitedly and independently slidable within the inner barrel member 12, lateral elongate longitudinal slots 110 are provided for receiving the pins 48 therein.

In use, the instrument 10 is positioned for taking of a biopsy specimen in such resting condition and the various components of the instrument 10 are then manipulated as will be described below to obtain the biopsy specimen.

Turning now to FIGS. 3-7, the interaction between the various components of the instrument 10, during its use, and in non-resting conditions thereof, is illustrated.

In FIG. 3, as illustrated, once the instrument 10 has been precisely positioned relative to the tissue within a body to be biopsied, a user of the instrument 10, using only one hand, maintains the position of the inner barrel member 12, such as between thumb and forefinger, and pulls rearwardly on the outer barrel member 14 with the other fingers of his hand until the detent 35 of the V shaped trigger 30, which has dragged along an upper surface of the reduced in thickness portion 72 of the latching indicator structure 34, falls into the groove 74 at the distal end of the latching indicator structure 34.

When such position is reached, bearing in mind the positioning of the distal end edge 108 of the flap 100 of the cannula driver 84, relative to the position of the groove 74, the user will hear an audible "click". The "click" is produced by a sudden upward motion of the flap 100 and engagement of the distal end 104 of the flap 100 within the cutout 76 of the inner barrel member 12, with the vertical distal end wall 106 of the flap 100 abutting against a distal end edge 112 of the cutout 76. Upon such engagement between the flap 100 and the inner barrel member 12, the spring 94 is expanded to a significant degree and maintained in such expanded state by the engagement between the flap 100 and the cutout 76. The flap 100 and cutout 76 form the latching mechanism 32 of the instrument 10.

It will be noted that since the outer barrel member 14 which is locked to the hub 56 of the stylet 22, is pulled rearwardly by a distance equal to the distance the cannula driver 84 is pulled back, the tip 23 of the stylet 22 remains within the tip 21 of the cannula 20, the cannula 20 having been moved proximally into the inner barrel member 12 from its outwardly advanced, at rest position by movement of the cannula driver 84 proximally within the inner barrel member 12.

In such condition of the instrument 10, relative movement between the inner and outer barrel members 12 an 14 can continue, with the position of the cannula driver 84 within the inner barrel member 12 now being "locked" by the latching mechanism 32 and the cannula driver 84 can now be considered "armed" for quickly returning the cannula 20 distally to its at rest position as described hereinafter.

FIG. 4 is a radial cross-sectional view through the instrument 10 and shows the longitudinal alignment of components when the instrument is armed as shown in FIG. 3.

Figure 5:
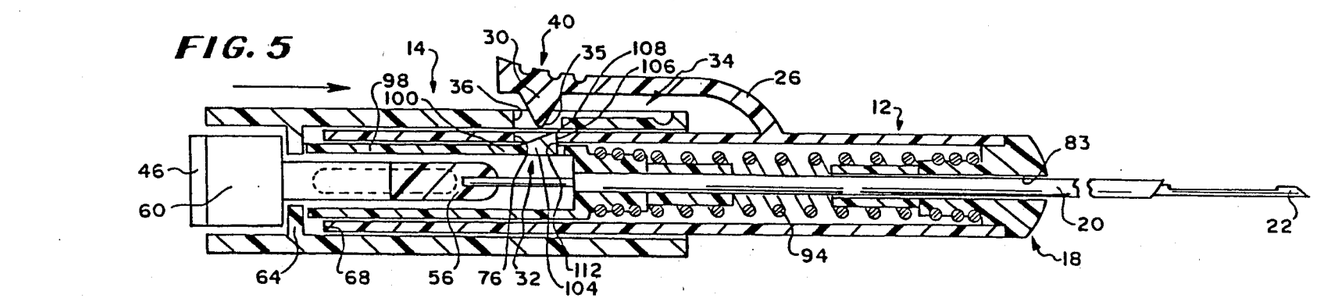
FIG. 5 is a longitudinal cross sectional view similar to FIGS. 2 and 3 and shows a stylet of the instrument being advanced distally.

Turning now to FIG. 5, the user of the instrument 10 then returns the outer barrel member 14 to its former position, moving it distally over the inner barrel member 12 until the detent 35 of the trigger 30 is again positioned within the cutout 36 at the proximal end of the latching indicator structure 34. Upon such forward or distal movement of the outer barrel member 14 over the inner barrel member 12, since the hub 56 of the stylet 22 is secured to the outer barrel member 14 as will be described below, the stylet 22 is also advanced distally out of the cannula 20, exposing the sampling notch 50 on the stylet 22.

Tissue surrounding the stylet 22 now falls into the exposed notch 50 of the stylet 22 and the user is ready to slice off the bit of tissue within the notch 50 from the surrounding tissue by use of the pointed tip 23 of the cannula 20 which will be quickly advanced distally over the stylet 22 and will act as a cutting edge for the instrument 10.

Figure 6:
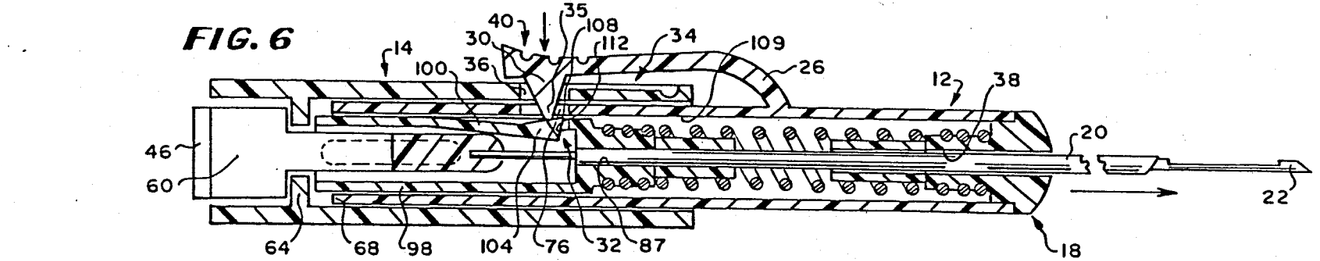
FIG. 6 is a longitudinal cross sectional view similar to FIG. 5 and shows a cannula of the instrument being projected distally over the advanced stylet upon actuation of a trigger of the instrument.

Turning now to FIG. 6, to accomplish such dissection of the tissue which has fallen into the notch 50, the user actuates the trigger 30 of the instrument 10 by depressing the proximal end portion 40 of the trigger 30. The detent 35 of the trigger 30 is moved downwardly through the cutout 36 in the outer barrel member 14, and into the cutout 76 in the inner barrel member 12, which is aligned directly beneath the cutout 36 in the outer barrel member 14 when the outer barrel member 14 is in its most distal at-rest position over the inner barrel member 12, and contacts the distal end portion 104 of the flap 100 which, as shown in FIG. 3, is biased against the distal end wall 112 of the cutout 76 of the inner barrel member 12. A continued downward force on the trigger 30 will force the distal end portion 104 of the flap 100 downwardly, and the vertical distal end wall 106 of the flap 100 is eventually released from its abutment against the distal wall 112 of the cutout 76. This disengagement of the flap 100 releases the latching mechanism 32 and thus spring 94 from its locked, extended condition and allows the spring 94 to quickly contract to its compressed, at rest condition. Such contraction of the spring 44 pulls distally on the first stepped portion 86 of the cannula driver 84 to which the spring 94 s attached and the cannula driver 84 rapidly advances the cannula distally over the tissue within the notch 50 and the user hears a "snap" produced by the second stepped section 92 of the cannula driver 84 hitting the second stepped section 90 of the plug 18, confirming distal movement of the cannula 20 over the stylet 22. The trigger 30 upon release of the downward force thereon also returns quickly to its at-rest position.

Figure 7:
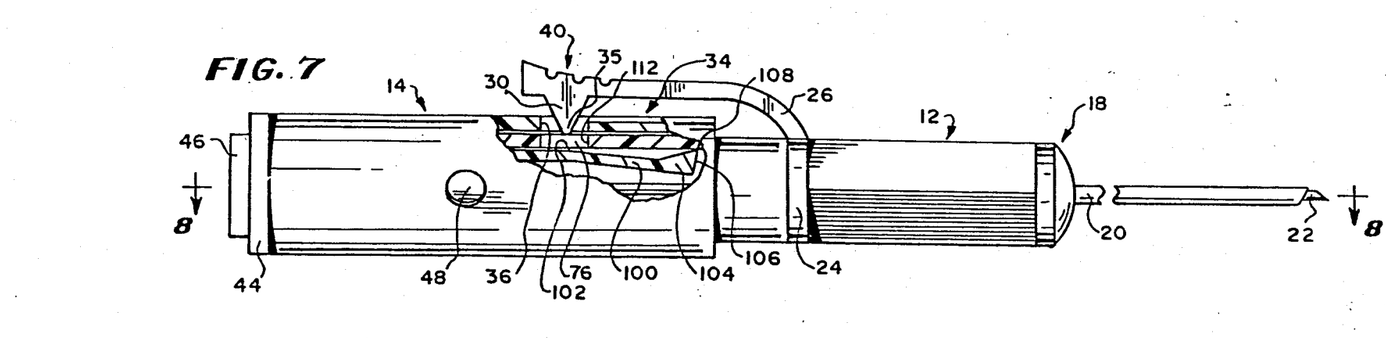
FIG. 7 is a perspective side view of the instrument, partly in section, and shows return of the instrument to an at rest condition upon release of the trigger.

Once the cannula 20 has been advanced quickly or "shot" over the stylet 22, it entraps a sheared tissue specimen within the specimen notch 50 and the instrument 10 is returned to its original at-rest condition, as shown in FIG. 7. As illustrated, the trigger 30 is again positioned within the cutout 36 in the outer barrel member 14, the cutout 36 in the inner barrel member 12 is again aligned directly under the cutout 76 in the outer barrel member 14, and the flap 100 of the cannula driver 84 once again is inwardly displaced, with the end edge 108 of the distal wall 106 resting lightly against the inner barrel member 12.

It is preferable, in any core biopsy instrument 10, to be able to remove the stylet 22 from the proximal end 42 of the instrument 10 without dislodging the cannula 20 from a particular position within a patient. A user may, for example, want to make sure that the tissue sample is adequate in size, or is from the correct location, prior to dislodging the entire instrument 10 from within the body of the patient. For this reason, as illustrated in FIGS. 8 and 9, the instrument 10 of the present invention is provided with a proximally removable stylet 22.

Figures 8, 9, 10:
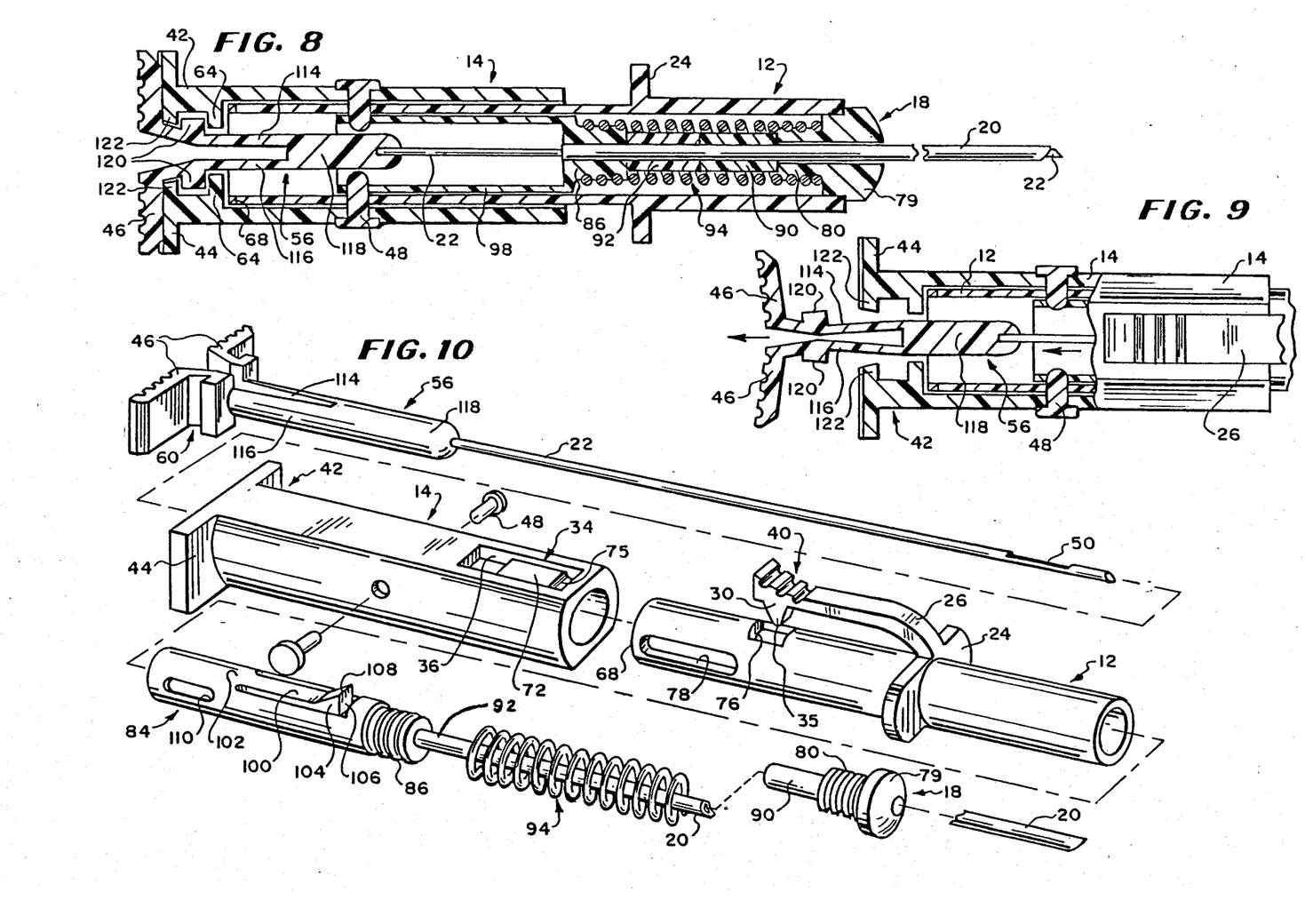
FIG. 8 is a longitudinal cross sectional top plan view of the instrument and shows tee proximal removable stylet and stylet hub of the instrument.
FIG. 9 is a top plan view, partly in section of a proximal end portion of the instrument and shows the stylet and stylet hub being removed proximally from the instrument.
FIG. 10 is an exploded perspective view of the biopsy instrument of the present invention.

As illustrated in FIG. 8, which is a cross sectional top plan view into the instrument 10, the stylet hub 56 has two laterally outwardly biased legs 114 and 116 which extend proximally from a bullet shaped distal end portion 118 of the hub 56. The legs 114 and 116 terminate proximally of the proximal end 42 of the outer barrel member 14. Each leg has one of the wings 46 extending laterally outwardly therefrom along the proximal end 42 of the flange 44 of the outer barrel member 14 and each wing 46 has the serrated proximal end face 47. These wings 46 can be moved toward each other, as illustrated in FIG. 9, to release a laterally outwardly extending rib 120 of each leg 114, 116 from entrapment between the peripheral rib 64 and two proximal inwardly extending flanges 122 which form an inward continuation of the rear flange 44 of the outer barrel member 14.

As shown in FIG. 9, when the wings 46 are pinched together, the ribs 120 are disengaged from entrapment between the peripheral rib 64 and the flanges 122 of the outer barrel member 14 and the stylet 22 can be removed from the proximal end 42 of the instrument 10 by pulling proximally on the stylet hub 56 until the stylet 22 exits the proximal end 42 of the instrument 10.

Likewise, if the stylet 22 must be reinserted, such as for obtaining a further sample, or obtaining a sample from a slightly different position, the user merely slides the stylet 22 and hub 56 therefor back into the instrument 10 until it "clicks" into engagement with the outer barrel member 14 as defined above, and the instrument 10 is ready to be used again.

In FIG. 10, the simplicity of the instrument 10 is illustrated in an exploded perspective view of the components of the instrument 10. As shown, the instrument 10 is comprised of four major components or sections; the outer barrel member 14; the inner barrel member 12 which is slidably received within the outer barrel 14; the cannula driver 84 including the cannula 20 which is slidably received within and extends distally outwardly of the inner barrel member 12; and the hub 56 mounting the stylet 22 which extends through the length of the instrument 10.

The instrument 10 is disposable and may be made of any suitable hard polymer, such as ABS. The cannula 20 and stylet 22, of course, are made of stainless steel. Also, although the barrel members 12 and 14 are illustrated as being somewhat polygonal in cross-section, this is not to be considered at all limiting.

Referring now to a second embodiment of the core biopsy instrument 200 shown in FIGS. 11-18 structures that are similar to those of the first embodiment 10 have been, for the most part, given like reference numerals for ease of description.

Figure 11:
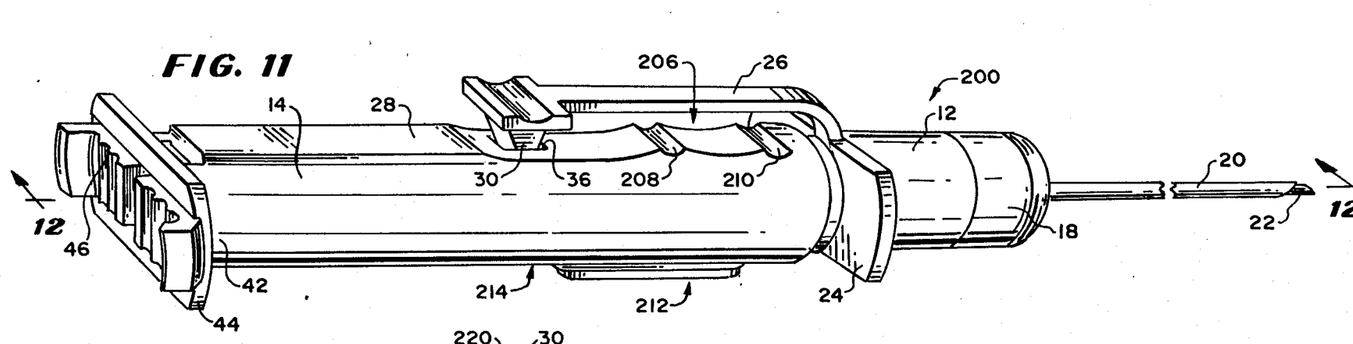
FIG. 11 is a perspective side view of another embodiment of the biopsy instrument of the present invention in an at-rest condition and shows a locating pin, which adjusts the length of the cannula advancement, in a first position thereof.

As shown, the instrument 200 has an inner barrel member 12 and an outer barrel member 14 which are substantially similar to those of the first embodiment of the instrument 10. The inner barrel member 12 has mounted at a distal end 16 thereof a nose or plug 18 through which a cannula 20 and needle 22 extend distally.

The inner barrel member 12 also has finger flanges 24 thereon and has an integral lever arm 26 originating on an upper surface 77 between the finger flanges 24 and extending proximally over the outer barrel member 14. The arm 26 has a trigger element 30, a detent 35 of which is to be received within a cutout 36 provided in the outer barrel member.

Figures 12, 13:
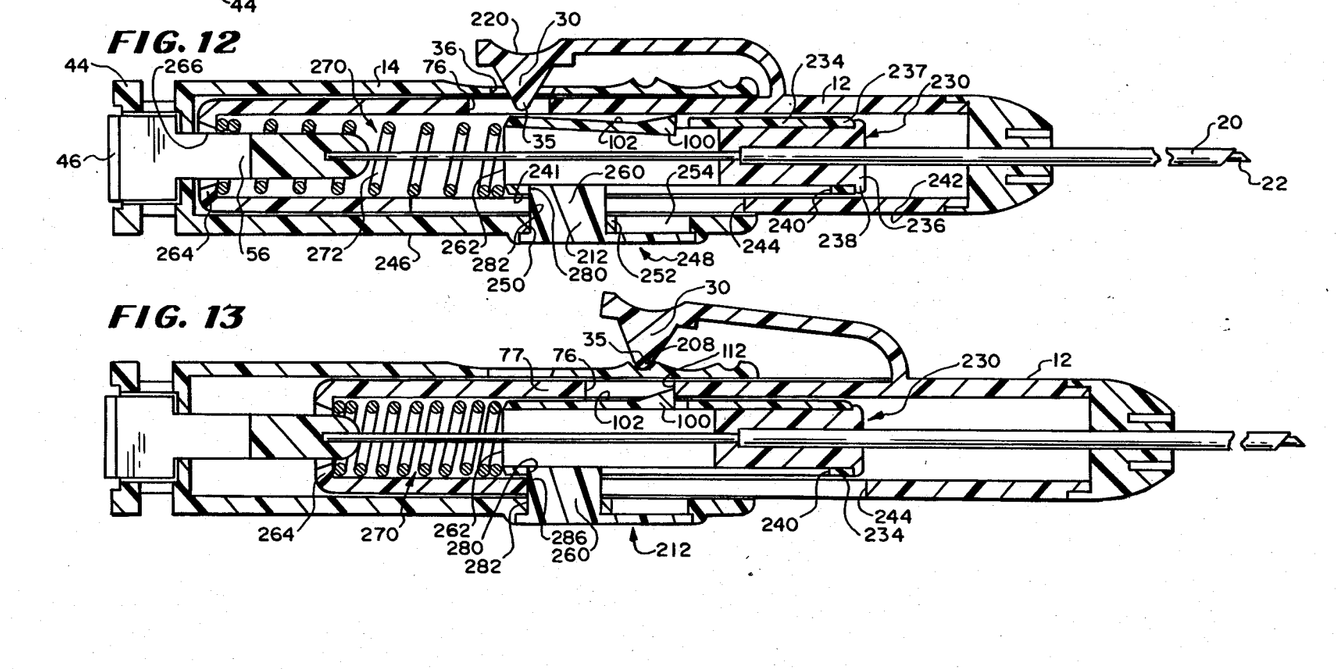
FIG. 12 is a longitudinal cross-sectional view through the instrument and is taken at line 12—12 of FIG. 11.
FIG. 13 is a longitudinal cross-sectional view similar to FIG. 12 and shows a cannula driver of the instrument being proximally biased.

The outer barrel member 14 is provided at its proximal end 42 with a proximal flange 44, and situated against the proximal flange 44 are two wings 46 of the stylet hub 56 (FIG. 12). The instrument 200 has slightly different latching indicator structure 206 o the upper surface 28 of the outer proximal barrel member 14 and in this embodiment two grooves 208 and 210, are provided for receiving the depending detent 35 of the trigger element 30 therein, as will be described hereinafter.

Also, as will be described hereinafter, the instrument 200 has a limiting mechanism 212 on an undersurface 214 thereof which is utilized to set the distance to which the cannula 20 can be advanced distally of the nose 18 of the instrument 200.

Turning now to FIG. 12, there is shown therein a longitudinal cross-sectional view through the instrument 200. As illustrated, the inner barrel member 12 fits snugly within the outer barrel member 14 and has a cutout 76 therein which, when the instrument 200 is in an at rest condition or position as shown, is aligned directly beneath the cutout 36 in the outer barrel member 14. The detent 35 of the trigger element 30 is received within the cutout 76 in the inner barrel member 12. To assist in utilizing the lever arm 26, the ever arm 26 is provided with a thumb tab 220 and depression of this thumb tab 220 provides a rapid distal advancement of the cannula 20, to be described.

Turning now to a modified cannula driver 230, the cannula driver 230 is an elongate cylindrical member or cylinder 234 which is slidably received within the inner barrel member 12. The cannula driver 230 has a forward plug or nose piece 236 frictionally held within a front end 237 of the cylinder 234, with overlapping forward edges 238 thereof extending to the periphery of the cylinder 234. The cylinder 234 also is provided with a distal terminating flap mechanism 100 on an upper surface 102 thereof and further includes an elongate slot 240 in a bottom surface 241 of the cylinder 134.

As will be described hereinafter, a bottom surface 242 of the inner barrel member 12 is also provided with a somewhat shorter in length slot 244 which coacts with the slot 240. The outer barrel member 14 also has in a bottom surface 246 thereof a longitudinal split slot 248 which has an outwardly flanged shoulder 250, with the slot 248 being bifurcated by a wall 252. Slot sections 254 on either side of the wall 252 are each of sufficient dimension to receive therein a pin 260 of the limiting mechanism 212 which extends upwardly into the instrument 200 first through one of the slot sections 254 in the outer barrel member 14, then through the slot 244 in the inner barrel member 12, and into the slot 240 in the cannula driver 130.

The limiting mechanism 212 produces a cooperative interaction between the cannula driver 230, the inner barrel member 12 and the outer barrel member 14, as will be described in greater detail hereinafter.

The cannula driver 230 has an open proximal end 262 and the inner barrel member 12 has a rear or proximal end wall 264. A bore 266 in the end wall 264 allows the stylet hub 56 to extend therethrough.

Between the proximal wall 264 of the inner barrel member 12 and the proximal end 262 of the cannula driver 230, a spring 270 is extended in such a manner that the stylet hub 56 and the stylet 22 mounted thereon extend distally within turns 272 of the spring 270, without obstruction. The spring 270 has a diameter approximately equal to the diameter of the cannula driver 230. If desired, the periphery of the cannula driver 230 around the open proximal end 262 thereof, can be angled, to provide a seat against and within which an end of the spring 270 can rest.

In this at rest condition or position of the instrument 200, with the pin 260 of the limiting mechanism 212 positioned in a proximal slot section 254 in the bottom surface 246 of the outer barrel member 14, the distance which the cannula diver 230 can move distally within the instrument 200 is limited by abutment of a proximal end wall 280 of the slot 240 in the cannula driver 230 abutting against a rear or proximal end wall 282 of the pin 260.

In "arming" or sitting of the instrument 200 for automatic actuation or advancement of the cannula driver 230, as illustrated n FIG. 13, the outer barrel member 14, is pulled proximally until the trigger element 30 of the lever arm 26 is received within the first notch 208 of the latching indicator structure 206.

Figure 14:
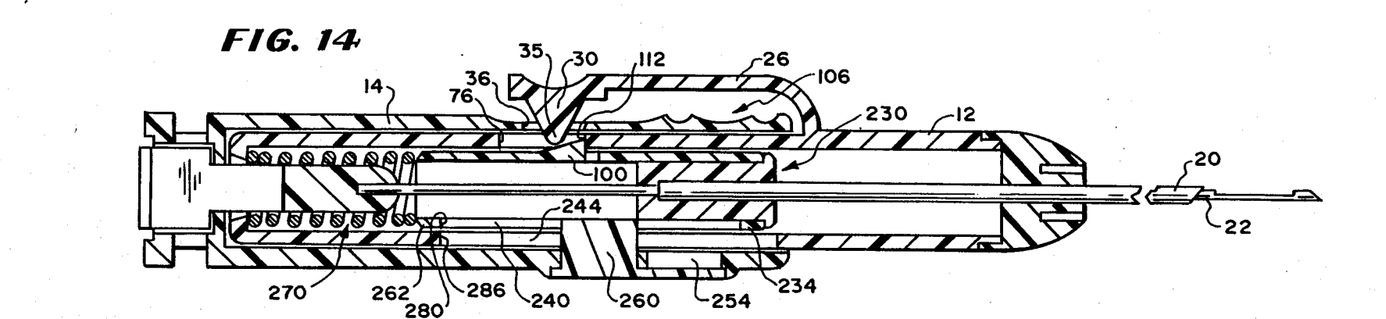
FIG. 14 is a longitudinal cross-sectional view similar to FIGS. 12 and 13 and shows a stylet of the instrument being advanced distally.

When the detent 35 o the trigger element 30 is received within the first or proximal groove 208, it will be seen that the flap 100 on the upper surface 102 of the cannula driver 230 is moved into engagement against the distal wall 112 of the cutout 76 in the upper wall 77 of the inner barrel member 12 and latches against the distal wall 112. When the barrel members 12 and 14 are positioned in such a manner, the pin 260 of the limiting mechanism 212 is positioned in abutment against a proximal wall 280 of the slot 240 in the cannula driver 230, and, is also positioned against a proximal end wall 286 of the slot 244 in the inner barrel member 12. Once latching of the flap 100 within the cutout 76 of the inner barre member 12 has taken place, a user of the instrument 200 returns or moves the proximal outer barrel member 14 distally until it is returned to its original position, similar to that shown in FIG. 12, with the flap 100 now being engaged within the cutout 76 of the inner barrel member 12 and now being positioned directly beneath the trigger element 30 of the lever arm 26, as shown in FIG. 14. It will also be noted that the spring 270, upon latching of the flap 100 within the cutout (FIG. 13) is compressed and is maintained in such a compressed state as shown in FIG. 14. Upon actuation or depression of the trigger element 30 of the lever arm 26, it will be noted that the flap 100 will be disengaged from abutment against the distal wall 112 of the cutout 76 in the inner barrel member 12 by action of the detent 35 and will, in turn, free the spring 270 from its compressed or contracted state, whereupon the spring 270 will push against the proximal end 262 of the cannula driver 230 and force she cannula driver 230, and cannula 20 mounted therein, distally, up to a point at which the proximal end wall 280 of the slot 240 in the cannula driver 230 strikes against the pin 260 of the limiting mechanism 212, stopping the distal movement of the cannula driver 230 at a predetermined point.

With the limiting mechanism 212 positioned as shown in FIGS. 12-14, it will be apparent that the length or distance of distal travel of the cannula driver 230 will be less than that which would be available if the limiting mechanism 212 were in a reversed position, rotated 180°, so that the pin 260 was received in the slot section 254 distal to the wall 252, to provide for a greater distance of travel for the cannula driver 230.

The operation and coaction of the structural elements within the instrument 200, when the pin 260 of the limiting mechanism 212 is positioned within the distal slot section 254 in the outer barrel member 14 is shown and will be described in connection with the description of FIGS. 15-17.

Figure 15:
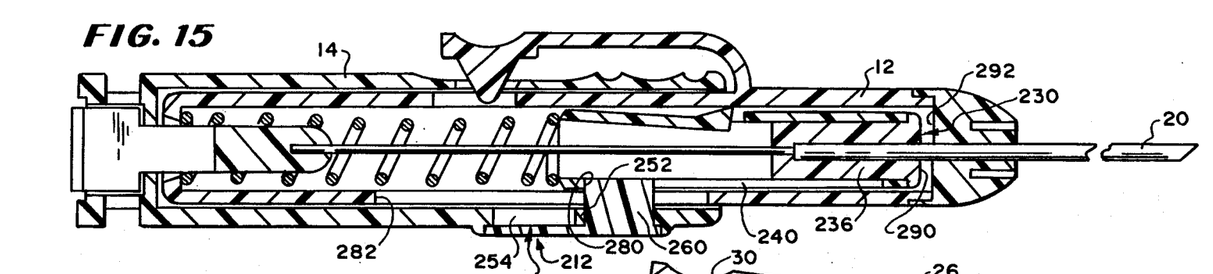
FIG. 15 is a longitudinal cross-sectional view similar to FIG. 12 and shows the locating pin a second position thereof.

In FIG. 15, the pin 260 of the limiting mechanism 212 has now been positioned in the distal slot section 254 in the outer barrel member 14 and, in the at rest position of the instrument 200, a proximal end wall 280 of the slot 240 in the cannula driver 230, which abuts the pin 260, is now positioned distally of the position shown in FIGS. 12-14 by a distance, D, equal to the longitudinal dimension of the pin 260 plus the longitudinal dimension of the wall 252 of slot 248 in the outer barrel member 14. A forward or distal end wall 290 of the nose or plug 236 of the cannula driver 230 now almost abuts against a proximal wall 292 of the nose or plug 18 of the instrument 200.

As will be appreciated, the cannula 20 which is mounted within the plug member 236 is advanced distally of the nose or plug member 18 by a distance which is greater than the distance advanced in FIGS. 12-14, also by the distance D.

During the process of "arming" the instrument 200, first of all, with the pin 260 in a distal position, upon pulling the outer barrel member 14 proximally away from the distal inner barrel member 12, the detent 35 of the trigger element 30, rather than moving into the proximal groove 208, may now be advanced into the distal groove 210 of the latching indicator structure 206 on the upper surface 28 of the outer barrel member 14.

In this respect, the two grooves 208 and 210 are separated by the distance D and, since the pin 260 of the limiting mechanism 212 is distally located, the outer barrel member 14 can be extended further proximally with the detent 35 of the trigger element 30 now falling into the notch 210. To assist in ease of movement of the detent 35 of the trigger element 30 along the upper surface 28 of the outer barrel member 14, an arcuate surface is provided to the latching indicator structure 206 between the notches 208 and 210. The ability of positioning of the detent 35 of the trigger element 30 within the distal groove 210 is indicative that the pin 260 is in the distal slot section 254 of the slot 248 in the outer barrel member 14.

In such position of the outer barrel member 14 relative to the inner barrel member 12, there is again a latching of the flap 100 of the cannula driver 230 within the cutout 76 of the inner barrel member 12, once again contracting the spring 270, setting or "arming" the cannula driver 230 for automatic advancement of the cannula 20 upon actuation of the trigger element 30.

Figure 17:
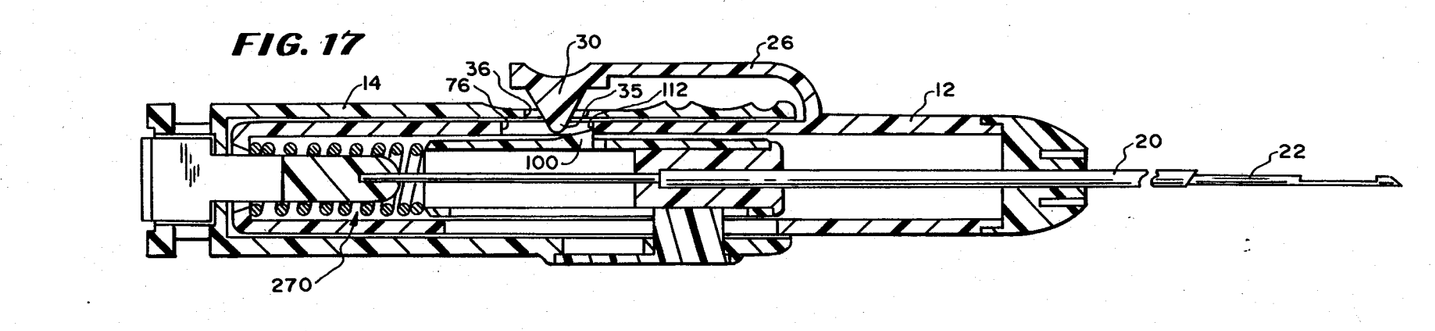
FIG. 17 is a longitudinal cross-sectional view similar to FIGS. 15 and 16 and shows a style of the instrument being advanced distally.

In FIG. 17, when the outer barrel member 14 is once again advanced distally, back to its previous position, the cutout 36 in the outer barre member 14 once again is aligned over the cutout 76 in the inner barrel member 12 and again, the detent 35 of the trigger element 30 of the lever arm 26 is in a position such that, upon depression, it will disengage the flap 100 from abutment against the distal wall 112 of the cutout 76 in the inner barrel member 12, allowing the spring 270 to return to its fully extended, at-rest state, forcing or shooting the cannula driver 230 distally and thus rapidly shooting or advancing the cannula 20 distally a predetermined distance, greater, by the distance D, than the distance that the cannula 20 is advanced when the pin 260 of the limiting mechanism 212 is in proximal slot section 254 (FIG. 14).

In this respect, when the flap 100 is disengaged from its engagement with the inner barrel member 12, the spring 270 returns to its non-compressed, at rest condition or state, forcing the cannula driver 230 distally. With the pin 260 of the limiting mechanism 212 received in the distal slot section 254 the cannula driver 230 may advance a distance which is greater than the distance advanced when the pin 260 is in the proximal slot section 254 as shown in FIG. 14, by the distance.

It will be understood that when the pin 260 of the limiting mechanism 212 is in a distal position, a different stylet 22' which has a length greater than the length of the stylet 22, by the distance D, is utilized with the instrument 200.

The engagement of the pin 260 in the distal slot section 254 allows the instrument 200 to take a biopsy from tissue which is located deeper than that which is biopsied when the pin 260 is in the proximal slot section 254. Accordingly, by the provision of the simple limiting mechanism 212, a biopsy instrument 200 can be provided which has a variable or settable depth of penetration for biopsy.

Figures 16, 18:
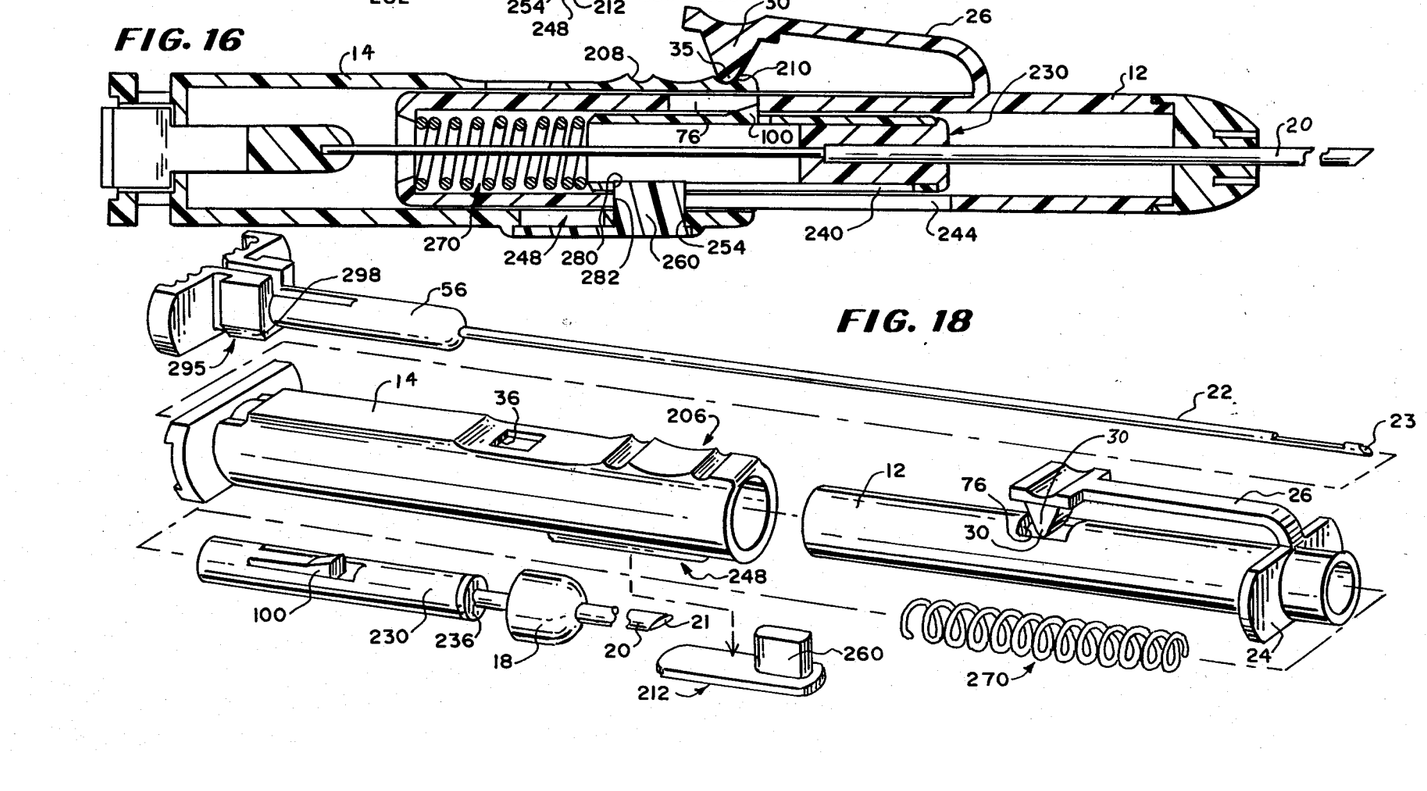
FIG. 16 is a longitudinal cross-sectional view similar to FIG. 15 and shows the cannula driver being proximally biased.
FIG. 18 is an exploded perspective view of the biopsy instrument shown in FIG. 11.

In FIG. 18, there is shown an exploded perspective view of the various components forming the biopsy instrument 200. The biopsy instrument first of all has a stylet 22 which is mounted on stylet hub 56. The stylet 22 and hub 56 are removably received within the outer barrel member 14 of the instrument 200. It is preferable, as shown in the Figure, to provide an orienting element 295 on the hub 56 of the stylet 22, here shown as an inwardly angled shoulder 298, which will allow the hub 56 to be latched within the outer barrel member 14 in one position only, the outer barrel member 14, although not shown, having an angled shoulder in the rear wall 44 thereof which complements the angled shoulder 298. The provision of the orienting element 295 guarantees that the point 23 of the stylet 22 is always positioned in opposed manner to the point 21 of the cannula 20.

The inner barrel member 12 is sized and configured to be slidably received within the outer barrel member 14 and has an open forward end for receiving the spring 270 and the cannula driver 230 therein.

The cannula driver 230 is sized and configured to be slidably received within the inner barrel member 12, has the cannula 20 mounted in a plug 236 thereof and extends distally through the nose or plug 18 of the instrument 200, the stylet 22 being slidingly received within the cannula 20. The open rear end wall 262 of the cannula driver 230 is also adapted to fit over the stylet hub 54, when necessary, and may be provided with an angled peripheral shoulder against which the spring 270 may seat, if desired.

The spring 270 which is positioned behind or proximal to the cannula driver 230 and is compressed between the rear periphery of the cannula driver 230 and the proximal wall 264 of the inner barrel member 12 by latching of the flap 100 of the cannula driver 230 within the cutout 76 in the inner barrel member 12. The spring 270, upon actuation of the trigger element 30, expands to a non-compressed state and pushes the cannula driver 230, and cannula 20 carried thereby, over the protruding distal tip 23 of the stylet 22.

Finally, received through the slots 248, 244, 240 in the bottom surfaces of the outer barrel member 14, the inner barrel member 12, and the cannula driver 230, respectively, is the pin 260 of the limiting mechanism 212, which allow the cannula 20 to be distally extended either a short distance or a greater distance, depending on the position of the pin 260, being positioned either proximally or distally, within the slot section 254 in the outer barrel member 14.

The method of using the biopsy instrument 10 or 200 is described in application Ser. No. 150,984 the disclosure of which is incorporated herein by reference.

The soft tissue core biopsy instrument 200 of the present invention has a number of advantages, some of which have been described above, and others of which are inherent in the invention. Also, modifications can be made to the instrument 200 without departing from the teachings of the present invention. For example, alignment elements, which coact between the hub 56 for the stylet 22 and the proximal end 42 of the outer barrel member 14, to ensure that the sampling notch 50 of the stylet 22 is properly oriented within the instrument 10, can be provided. Accordingly the scope of the invention is only to be limited as necessitated by the accompanying claims.

I claim:

1. A soft tissue core biopsy instrument comprising:
   a proximal outer barrel member having a distal end and a proximal end;
   a distal inner barrel member which is slidably received within said outer barrel member and which has a distal end and a proximal end;
   a cannula driver in said inner barrel member;
   a cannula extending distally from said inner barrel member, being fixed to said cannula driver, and having a distal tip, said cannula driver being slidably received and movable within said distal inner barrel member and said cannula extending a predetermined distance out of said distal end of said inner barrel member when the instrument is in an at rest condition;
   a stylet having a distal end, a distal end portion, a proximal end, and being removably received in said outer barrel, in said inner barrel, and in said cannula, said distal end portion having a biopsy sample receiving notch therein;
   a stylet hub mounted to said proximal end of said stylet, said stylet hub being removably attached to the proximal end of said proximal outer barrel member to enable multiple biopsies to be obtained with one insertion of said cannula,
   said stylet extending distally from said hub and within said cannula with said distal end portion (a) being positioned within said cannula when the instrument is in an at rest position and (b) extending distally of said distal tip of said cannula in position to capture a biopsy sample when the instrument is in a cocked position;
   biasing means within said inner barrel member for biasing said cannula driver toward the distal end of said inner barrel member;
   latching means associated with said cannula driver and said inner barrel member for latching said cannula driver in a proximally retracted cocked position within said outer barrel member and said inner barrel member against the biasing action of said biasing means;
   a trigger, associated with said latching means, for unlatching said latching means, said trigger, upon being actuated for unlatching of said latching means, allowing said biasing means to quickly return said cannula driver and said cannula to said at rest distally extending position thereof and over said stylet distal end portion.

2. A soft tissue core biopsy instrument comprising:

a proximal outer barrel member having a distal end and a proximal end;

a distal inner barrel member which is slidably received within said outer barrel member and which has a distal end and a proximal end;

a cannula driver in said inner barrel member;

a cannula extending distally from said inner barrel member, being fixed to said cannula driver, and having a distal tip, said cannula drive being slidably received and movable within said distal inner barrel member and said cannula extending a predetermined distance out of said distal end of said inner barrel member when the instrument is in an at rest condition;

a stylet having a distal end, a distal end portion, a proximal end, and being removably received in said outer barrel, in said inner barrel, and in said cannula, said distal end portion having a biopsy sample receiving notch therein;

a stylet hub mounted to said proximal end of said stylet; said hub being removably attached to the proximal end of said proximal outer barrel member to enable multiple biopsies to be obtained with one insertion of said cannula, said stylet extending distally from said hub and within said cannula with said distal end portion (a) being positioned within said cannula when the instrument is in an at rest position and (b) extending distally of said distal tip of said cannula in position to capture a biopsy sample when the instrument is in a cocked position;

biasing means within said inner barrel member for biasing said cannula driver toward the distal end of said inner barrel member;

latching means associated with said cannula driver and said inner barrel member for latching said cannula driver in a proximally retracted position within said outer barrel member and said inner barrel member against the biasing action of said biasing means;

a trigger, associated with said latching means, for unlatching said latching means, said trigger, upon being actuated for unlatching of said latching means, allowing said biasing means to quickly return said cannula driver and said cannula to said at rest distally extending position thereof and over said stylet distal end portion; and means for selectively limiting the distally extending position of said cannula.

3. The instrument of claim 2 wherein said outer barrel member has a longitudinal slot therein, said inner barrel member has a longitudinal slot therein, and said cannula driver has a longitudinal slot therein and said cannula position limiting means being received in said longitudinal slots.

4. The biopsy instrument of claim 2 wherein said cannula position limiting means comprise an elongate planar base portion having two sides and a pin extending from one side of said base portion.

5. The biopsy instrument of claim 4 wherein said pin has a width slightly less than on half of a longitudinal dimension of said elongate base portion.

6. The biopsy instrument of claim 5 wherein said longitudinal slot in said outer barrel member is bifurcated into two longitudinal slot sections and said pin fits snugly within either slot section.

7. The instrument of claim 6 further including latching indicator means on said outer barrel member for indicating the slot section within which said pin of said position limiting means is received.

8. The biopsy instrument of claim 4 wherein said base portion of said position limiting means is releasably fixed within a recess in the outer wall surface of said outer barrel member.

9. The biopsy instrument of claim 8 wherein said position limiting means is removable from said recess whereby said pin can be positioned to extend into one of the other of said slot sections, and said base portion extends over and covers both slot sections.

10. A soft tissue core biopsy instrument comprising:
a proximal outer barrel member having a distal end and a proximal end;

a distal inner barrel member which is slidably received within said outer barrel member and which has a distal end and a proximal end, said proximal end including a proximal wall;

a cannula driver located in said inner barrel member and having a proximal end and a distal end;

a cannula extending distally from said inner barrel member, being fixed to said cannula driver, and having a distal tip, said cannula driver being slidably received and movable within said distal inner barrel member and said cannula extending a predetermined distance out of said distal end of said inner barrel member when the instrument is in an at rest condition;

a stylet having a distal end, a distal end portion, a proximal inner barrel, and in said cannula, said distal end portion having a biopsy sample receiving notch therein;

a stylet hub mounted to said proximal end of said stylet; said stylet hub being removably attached to the proximal end of said proximal outer barrel member to enable multiple biopsies to be obtained with one insertion of said cannula, said stylet extending distally from said hub and within said cannula with said distal end portion (a) being positioned within said cannula when the instrument is in an at rest position and (b) extending distally of said distal tip of said cannula in position to capture a biopsy when the instrument is in a cocked position;

biasing means within said inner barrel member for biasing said cannula driver toward the distal end of said inner barrel member, said cannula driver biasing means comprising a spring located within said inner barrel member between said proximal wall of said inner barrel member and said proximal end of said cannula driver;

latching means associated with said cannula driver and said inner barrel member for latching said cannula driver in a proximally retracted position within said outer barrel member and said inner barrel member against the biasing action of said biasing means;

a trigger, associated with said latching means, for unlatching said latching means, said trigger, upon being actuated for unlatching of said latching means, allowing said biasing means to quickly return said cannula driver and said cannula to said at rest distally extending position thereof and over said stylet distal end portion.

11. The instrument of claim 10 wherein said proximal wall of said inner barrel member has a central throughbore therein within and through which said stylet hub may be slidably received.

12. The instrument of claim 10 wherein said cannula driver is a hollow tubular structure having said cannula mounted within said distal end therof by a plug frictionally engaged within said tubular structure and wherein said proximal end of said cannula driver is open to allow sliding of the proximal end over and about said stylet hub.

13. The instrument of claim 10 wherein said spring has a diameter sufficient to allow said spring to slide over said stylet hub and to allow said spring to expand and contract within said inner barrel member without obstruction.

* * * * *

UNITED STATES PATENT AND TRADEMARK OFFICE
CERTIFICATE OF CORRECTION

PATENT NO. : 4,907,599
DATED : March 13, 1990

Page 1 of 2

INVENTOR(S) : Glenn N. Taylor

It is certified that error appears in the above-identified patent and that said Letters Patent is hereby corrected as shown below:

Column 1, line 57, "tee" should be --the--.

Column 2, line 18, "tee" should be --the--.

Column 4, line 14, "tee" should be --the--;

line 68, "rm" should be --arm--.

Column 5, line 42, "ed" should be --end--;

line 45, "nd" should be --and--.

Column 7, line 56, "an" should be --and--.

Column 8, line 40, "44" should be --94--;

line 42, "s" should be --is--.

Column 10, line 7, "o" should be --on--;

line 26, "ever" should be --lever--.

Column 11, line 17, "n" should be --in--.

UNITED STATES PATENT AND TRADEMARK OFFICE
CERTIFICATE OF CORRECTION

PATENT NO. : 4,907,599
DATED : March 13, 1990
INVENTOR(S) : Glenn N. Taylor

Page 2 of 2

It is certified that error appears in the above-identified patent and that said Letters Patent is hereby corrected as shown below:

line 21, "o" should be --of--;

line 34, "barre" should be --barrel--;

line 52, "she" should be --the--.

Column 12, line 53, "barre" should be --barrel--.

Column 15, line 61, "on" should be --one--.

Signed and Sealed this

Twenty-ninth Day of December, 1992

Attest:

DOUGLAS B. COMER

Attesting Officer

Acting Commissioner of Patents and Trademarks